United States Patent
Stewart (10) Patent No.: US 6,235,016 B1
(45) Date of Patent: May 22, 2001

(54) METHOD OF REDUCING SEBUM PRODUCTION BY APPLICATION OF PULSED LIGHT

(76) Inventor: Bob W. Stewart, 5745 Pandora Ave., Cincinnati, OH (US) 45213

(*) Notice: Subject to any disclaimer, the term of this patent is extended or adjusted under 35 U.S.C. 154(b) by 0 days.

(21) Appl. No.: 09/270,327

(22) Filed: Mar. 16, 1999

(51) Int. Cl.[7] .................................................. A61B 18/18
(52) U.S. Cl. ..................................... 606/9; 606/2; 606/13; 606/17
(58) Field of Search ............................ 606/2, 3, 9–11, 606/13, 16, 17

(56) References Cited

U.S. PATENT DOCUMENTS

| 3,538,919 | 11/1970 | Meyer . |
| 4,388,924 | 6/1983 | Weissman et al. . |
| 4,617,926 | 10/1986 | Sutton . |
| 5,226,907 | 7/1993 | Tankovich . |
| 5,304,170 | * 4/1994 | Green . |
| 5,405,368 | * 4/1995 | Eckhouse . |
| 5,464,436 | 11/1995 | Smith . |
| 5,595,568 | 1/1997 | Anderson et al. . |
| 5,632,741 | 5/1997 | Zavislan et al. . |
| 5,647,866 | 7/1997 | Zaias et al. . |
| 5,817,089 | 10/1998 | Tankovich et al. . |

* cited by examiner

Primary Examiner—John Mulcahy
Assistant Examiner—Roy Gibson (57) ABSTRACT

A method of reducing sebum production in human skin, used primarily for cosmetic purposes, including the prevention of acne vulgaris, comprising the use of pulsed light having a wavelength, if monochromatic, or a wavelength range, if produced by a filtered non-monochromatic source, which targets the lipids contained within the sebaceous gland, thus destroying the differentiated and mature sebocytes by photothermolysis without damage to the surrounding and overlying tissue or to the basement membrane of the sebaceous gland.

27 Claims, 5 Drawing Sheets

Figure 5
Sebum Absorption Spectrum

METHOD OF REDUCING SEBUM PRODUCTION BY APPLICATION OF PULSED LIGHT

BACKGROUND OF THE INVENTION

1) Field of the Invention

The invention relates to a system for the selective photothermolysis of the sebaceous glands and/or sebum-covered structures located in the dermal portion of the human skin. The system is advantageously used to disrupt the production of sebum in portions of the skin afflicted with acne, thereby reducing or eliminating the severity of the condition without the regular intake or regular topical application of drugs and without permanently destroying the sebaceous glands. The system can also be used to treat folliculitis, ringworm, and seborrhea.

2) Description of the Prior Art

Acne vulgaris is the most common skin disease, affecting nearly 80% of young adults aged 11 to 30. Not only can it cause disfiguration and permanent scarring, but it can have an adverse effect on psychological development, often resulting in profound emotional scarring. This may in turn lead to social phobias, withdrawal from society, and to clinical depression.

Research during the past thirty years has confirmed the multifactorial origins of the disease. The three factors leading to the development of acne are: 1) excessive sebum production, 2) abnormal desquamation of sebaceous follicle epithelium, or comedogenesis and, 3) the proliferation of the bacterium Propionibacterium acnes. If any of these factors are absent, acne vulgaris will not result. Treatments have been developed which attack one of the three key factors in the attempt to disrupt the process leading to acne. To date, however, most if not all rely upon a drug regimen, delivered either topically or internally. Side effects resulting from these treatments are sometimes minor but can be quite serious.

Tankovich, et al in U.S. Pat. No. 5,817,089 teach an apparatus for the treatment of acne and seborrhea. Their approach involves waxing the hair from the duct or otherwise opening the duct in order to allow a carbon-based solution to penetrate into the duct. After full penetration of the solution into the sebaceous gland or in the vicinity of the gland, laser irradiation vaporizes the carbon particles leading to the full or partial destruction of the basement membrane (the epithelium tissue of the Tankovich, et al teachings). This leads to the reduced sebum production needed for treatment of acne or seborrhea.

The invention taught herein relies upon the reduction of the production of sebum in the affected areas as the key to prevention of acne vulgaris and/or seborrhea. By prudent choice of laser wavelength, pulse parameters (i.e., power, pulse duration), and intensity, the laser can be utilized to selectively disrupt the productivity of the sebaceous glands in the targeted area without significant injury to surrounding dermal tissue or to the sebaceous glands' basement membrane. Optimally, the period of time which the sebaceous gland requires in order to repair its production capability will be on the order of two (2) months or longer. In the event that a large percentage of the sebaceous glands in the affected area are sufficiently disrupted, the incidence of acne vulgaris and/or seborrhea will be significantly reduced in the treated area for several months. Repeated treatment will enable the attending physician to successfully treat the patient without frequent application of drugs. As the sebaceous gland is not permanently destroyed, the patient will have normal natural skin protection in later life. The normal drop-off in sebum production experienced by most individuals upon maturation will signal a cessation of the laser treatments.

SUMMARY OF THE INVENTION

Accordingly, it is a primary objective of the invention to provide an improved means of treating acne vulgaris and/or seborrhea, one which does not involve the consumption or topical application of substances which can result in undesirable side effects.

Another object of the invention is to provide a means of treating acne vulgaris and/or seborrhea which is substantially pain free and which does not result in hypotropic or hypertropic pigmentation, or in cosmetic scarring.

Another object of the invention is to provide a means of treating acne vulgaris and/or seborrhea which is semi-permanent in longevity, "semi-permanent" being defined in this context as being effective, without follow-up treatment, in preventing recurrence of acne vulgaris and/or sebonfhea in the treated regions for periods of several weeks to several months without any permanent damage to the sebaceous gland system.

Another object of the invention is to provide a means of treating acne vulgaris and/or seborrhea which is both cost effective for the individual dermatologist to obtain for his/her practice and for the patient who may be without the benefit of third-party payment for the physician's services.

Another object of the invention is to provide a means of treating ringworm and/or folliculitis which does not involve the intake of antibiotics or the topical application of prescription drugs.

The forgoing objects are basically attained by providing an apparatus for selectively delivering energy to the sebaceous gland in order to photocoagulate a sufficient number of the sebum-producing cells such that the sebum production in the targeted area is insufficient to lead to a return of acne vulgaris and/or seborrhea for a period of several weeks to several months.

The foregoing objects are also attained by providing an apparatus which delivers the energy to the sebaceous gland in a time period short enough to avoid heating of the surrounding tissues, yet long enough to avoid photoacoustic damage to those same surrounding tissues.

The foregoing objects are also attained by providing an apparatus which can be constructed using diode lasers as the excitation source, these lasers being durable, relatively user-friendly, and lightweight; as well as having a low cost-to-output power ratio and a long lifetime. Diode laser-based systems may be air-cooled and 110–120 VAC-powered, eliminating the need for more expensive power and cooling connections. Diode laser-based systems will not require a laser technician to operate, thus reducing the overhead costs associated with their use even further. InGaAs diode lasers have outputs in the 900–1100 nm wavelength range and power levels sufficient for dermatological applications. InGaAsP diode lasers have outputs in the 1.2–1.6 nm wavelength range. Although they currently have more limited output power levels, developments in the near future may result in powers sufficient for dermatological applications. Additionally, other laser systems, such as the Cr:$Mg_2SiO_4$, or forsterite, laser, have outputs in the desired wavelength ranges.

The foregoing objects are also attained by providing an apparatus which can be constructed without using lasers.

Filtered, low energy Xenon flashlamp systems can be used to provide light in the 900–1300 nm range which is suitable for selective photothermolysis of sebaceous glands without risking damage to overlying and surrounding tissues.

Other objects, advantages, and salient features of the present invention will become apparent from the following detailed description, which, taken in conjunction with the annexed drawings, discloses a preferred embodiment of the invention.

DRAWINGS

Referring now to the drawings which form a part of this original disclosure.

DRAWING REFERENCE NUMERALS

1—Basement membrane of Sebaceous Gland
2—Undifferentiated Cells
3—Differentiated Cells
4—Mature Sebocytes
5—Sebum
6—Sebaceous Gland Duct
9—hair
10—hair shaft
1—hair papilla
1—hair follicle
2—papillary vessel
3—sebaceous gland
4—epidermis
5—dermis
6—light beam
19—handpiece tip
20—intrafollicular probe

DESCRIPTION OF THE INVENTION

There are three factors involved in the development of acne. If any of the three is missing, the condition will not be present. These factors are: 1) excessive sebum production; 2) abnormal desquanation of the sebaceous follicle epithelium (comedogenesis); and 3) proliferation of P. acnes, resulting in inflammation. Seborrhea is also the result of excessive sebum production. The present invention is used to eliminate the excessive production of sebum.

In humans, the increased activity of the sebaceous glands is due in large part to the increase in dihydrotestosterone (DHT) available to the sebocytes. DHT is metabolized from testosterone (T) via the enzyme 5 alpha-reductase. The major sites for the testosterone/ 5 alpha-reductase activity in humans are: 1) the prostate (Type II), in the human male; 2) the apocrine sweat glands (Type I); and 3) the sebaceous glands (Type I). The hair follicles exhibit a significantly lower activity than the sebaceous gland and contribute only marginally to the body's total activity. The prostate is responsible for approximately ⅔ of the circulating DHT in males, with the apocrine and sebaceous glands responsible for the bulk of the remainder.

The activity of DHT metabolism is important in the study of the mechanisms behind the condition of acne. First, the androgen DHT induces proliferation of both facial and non-facial sebocytes. T also induces proliferation of facial sebocytes but inhibits proliferation of non-facial sebocytes. DHT is more effective than T in induction of proliferation of facial sebocytes. 5 alpha-reductase, which is responsible for the conversion of T into DHT, is found in the cytoplasm of facial sebocytes.

Cultured sebocytes strongly express Type I 5 alpha-reductase activity and metabolize T into DHT, along with other metabolites. This results in sebocytes proliferating probably via a non-feedback-regulated process. Furthermore, DHT, along with naturally-found linoleic acid, act to cause the undifferentiated sebocytes to differentiate into the lipid-producing, and T-metabolizing, sebocytes. The cycle continues, regulated mainly by the limitations on access to circulating lipids experienced by the mature sebocytes.

In order to appreciate the present invention, one must have some idea of the anatomy of the pilosebaceous unit and of the sebaceous gland itself. The pilosebaceous unit is composed of sebaceous glands and a hair follicle. The two are physically connected and usually vary inversely in their relative sizes, that is the larger the hair follicle, the smaller the sebaceous glands and vice versa. There are approximately 900 sebaceous glands per $cm^2$ on the face, upper neck, and chest. Some sebaceous glands do not have an associated hair follicle. Units that either have no hair follicle or only a small hair follicle are referred to as "sebaceous follicles".

Sebaceous glands are relatively simple, having partially-divided saccules with relatively wide mouths and little or no duct. Around the periphery of the saccule a well-defined basement membrane is present. The saccule is composed of undifferentiated, differentiated, and mature cells (sebocytes). The periphery of the saccule has undifferentiated cells located adjacently to the basement membrane. As new cells are formed and push older cells toward the sebaceous duct, the older cells develop into differentiated lipid-containing cells. The mature cells have an even higher concentration of lipids, leading to cell membrane disintegration and to the formation of sebum. The body's production rate of sebum varies over the lifetime of the individual. The maximum secretion rate is about 5.5 mg lipid per 10 $cm^2$ per 3 hours with a maximum average value of about 3.0 mg lipid (10–19 years of age). Production rate falls with age and may be a slow as 0.7–1 mg lipid in the elderly.

The role of sebaceous secretions on the surface of the skin would appear to be twofold: 1) the protection of the slkn by inhibition of water loss and the invasion of the skin by bacteria and fungi by means of an outer oily layer covering the skin 2) the provision of aromatic substances possibly associated with rudimentary sexual attraction.

Surveys have shown that 90% of women believe that their primary skin problem is dry skin. They seek moisturizing creams and lotions for relief. Seblum, by preventing or inhibiting the evaporation on of water that diffuses through the epidermal surface thus provides benefit in the treatment ofdry skin. The dry skin condition is also called xerosis.

Detergents might be expected to induce xerosis by removing the sebum, but the solvents which remove free surface lipids fail to have a lasting effect since the lipids are restored within a few hours as long as the sebaceous glands are functioning properly. However, if the sebaceous glands are permanently destroyed, a variety of skin disorders, including eczema, can result. This is due to the fact that removal the surface lipids increases the permeability the surface of the skin, increasing the penetration of the skin by a variety of both cationic and anionic surfactants.

Figure 2:
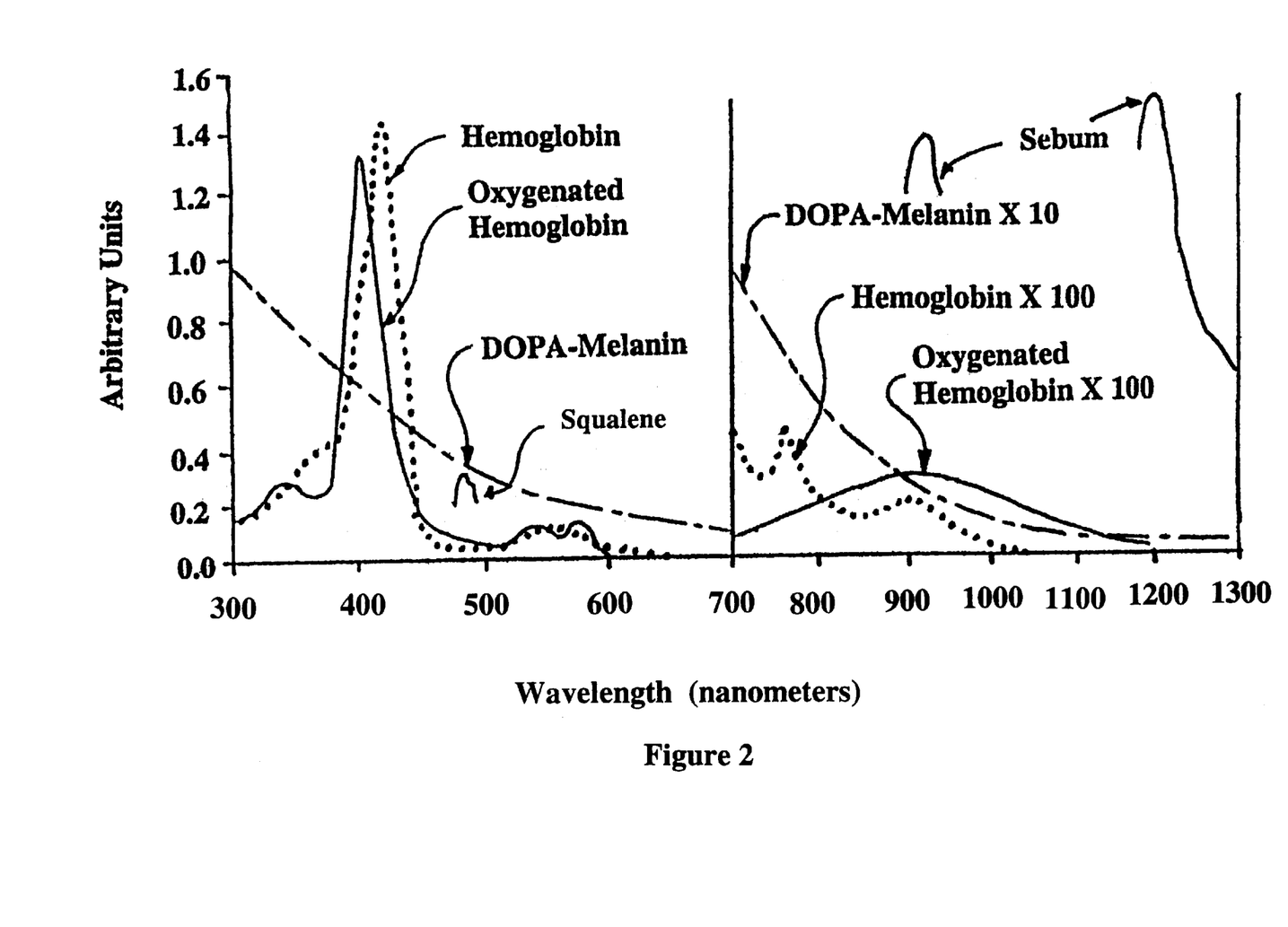
FIG. 2 is the absorption spectra of the major chromophores found in skin, minus water, in the visible-to-NIR portion of the electromagnetic spectrum.

It would appear that permanent destruction of the sebaceous glands of the face in order to prevent acne in one's youth could lead to a lifetime of other cosmetic problems, including xerosis and eczema The composition of sebum is well-known. Sebum is basically composed of disintegrated sebocytes, with keratin and lipids the major components. Of the lipids, triglycerides make up the bulk, with free fatty acids, wax esters, and squalene present in significant amounts. Triglycerides are esters of glycerol containing three fatty acids. Fatty acids are long-chained monocarboxylic acids, released from fat by hydrolysis. Wax esters are esters of a long-chained alcohol and a fatty acid. The molecular structure of these components of sebum all lend themselves to strong absorption in the near IR, with the absorption peaks dominated by the absorption by the triglycerides and free fatty acids around 920 nm, 1200 nm, and 1725 nm. Table 1 shows the relative composition of sebum. FIG. 2 shows the absorptions in the near IR. In addition to absorbing light in the NIR, at least one component of sebum, squalene, also has at least one local absorption peak in the visible. This absorption peak is centered around 480 nm.

The prior art related to the prevention of excessive sebum production has shown evidence of some success but the results are accompanied by side effects. These approaches have been primarily drug-based. Androgen-antagonists have been used with some degree of success. Their application is based upon the observation that the onset of excessive sebum production usually coincides with the onset of higher levels of the body's production of androgens. Efficacy is mixed, varying unpredictably from individual-to-individual. Side effects are to be expected as androgens are also related to the development of many desirable secondary sexual characteristics. The FDA has approved Accutane™ as a treatment for acne, as well. Unfortunately this drug has been linked to skin/hair side effects, especially to excessive dryness in these areas. More importantly, the drug has been linked to birth defects in births to women who have taken the drug during the pregnancy. As a woman who is taking the drug may become pregnant and, without being aware of her condition, continue to take the drug for several months before discovering her condition, this side effect is particularly important.

Additionally, efforts to treat acne have taken the approach of controlling the effects of P. acnes. Antibiotics have been utilized to this end with varying degrees of success. The health care community has recently become alarmed at the increasing number of antibiotic-resistant strains of micro-organisms. Any approach to preventing or controlling acne without the use of antibiotics would aid the situation by reducing the risk of the development of antibiotic resistance in common micro-organisms.

Lasers have been used successfully for a variety of medical applications. In some applications, the laser beam passes through the overlying tissue before reaching its target. In this approach, the wavelength of the laser beam and the absorption spectrum of the overlying tissue are such that the laser beam interacts with the target tissue as desired without undue damage to the surrounding tissue. In other applications, the laser beam is delivered directly to the target tissue via, for instance, an endoscope. In this case, the absorption spectrum of the overlying tissue is of little consequence. For dermatological laser applications, particularly those that involve the sebaceous or pilosebaceous follicles to some extent, the word "transcutaneous" describes the former approach. If the laser beam delivery is, for instance, through a small diameter waveguide inserted into the follicle, the word "intrafollicular" is often used to describe the approach.

The present invention makes use of selective photothermolysis in order to coagulate the differentiated and mature sebocytes located within the sebaceous gland In this manner, production of sebum will cease until the undifferentiated cells further mature. Selective photothennolysis can be achieved by one or more of the following approaches: 1) a choice of the wavelength of the light pulse that provides good absorption by the target sebocytes yet is such that only minimal absorption by the epidermis and non-targeted dermal chromophores (i.e., melanin and major blood components) results; 2) a judicious choice of the means to deliver the light pulse such that the energy is deposited mainly in the vicinity of the sebaceous gland, by-passing the overlying tissue (the intrafollicular approach) and thus avoiding absorption by the epidermis, and non-targeted dermal chromophores (i.e., melanin and major blood components); and/or 3) the use, either externally-applied (i.e., topically-applied) or intrasystemically-applied, of exogenous chromophores, together with the use of a wavelength of light which is well-absorbed by the chosen exogenous chromophore(s), yet is only minimally-absorbed by the undifferentiated sebocytes, the epidermis, and non-targeted dermal chromophores (i.e., melanin and major blood components). The present invention utilizes one of the first two approaches to achieve selective photothermolysis. Furthermore, the present invention achieves selective photothermolysis by choice of the duration of the light pulse such that it is long enough in order to avoid photoacoustic damage to the epithelial basement membrane surrounding the sebaceous gland saccules and other nearby tissues, yet short enough to enable coagulation of the target sebocytes without accompanying irreversible thermal damage to any proximal tissues. Furthermore, in one embodiment, the present invention employs a beam of light, the diameter of which is sufficiently large to enable coagulation of the targeted sebocytes in multiple sebaceous glands, simultaneously, yet small enough to allow the operator to treat only the portions of the patients' skin in which excessive sebum production is found. Furthermore, the present invention enables the operator to treat excessive sebum production during the adolescence of the patient without irreparable damage to the sebaceous gland network that would result in excessive skin dryness in mid-life and later years, yet produce sufficient damage to the target sebocytes results that even the most active sebum-producing patient will not require follow-up treatment for a period of several months.

Tankovich, et al in U.S. Pat. No. 5,817,089 teach an apparatus for the treatment of acne and seborrhea Their approach involves waxing the hair from the duct or otherwise opening the duct in order to allow a carbon-based solution to penetrate into the duct. After full penetration of the solution into the sebaceous gland or in the vicinity of the gland, laser irradiation vaporizes the carbon particles leading to the full or partial destruction of the basement membrane (the epithelium tissue of the Tankovich, et al teachings). This leads to the reduced sebum production needed for treatment of acne or seborrhea.

The apparatus taught herein differs from that taught by Tankovich, et al on several points. As no "contaminants" are required, the present invention does not require the hair to be removed or the duct to be emptied, in order to allow the contaminant to penetrate the duct. In fact, as the target is sebum itself, cleansing the duct and the gland of sebum would result in an ineffective treatment. The present invention does not require a waiting period between the application of the contaminant and the laser irradiation. Application of the present invention does not involve the risk of an inadvertent "tattoo" resulting from the microscopic explosions involved with the irradiation of the carbon particles, as taught by Tankovich, et al. These explosions, in addition to rupturing the basement membrane of the sebaceous glands, could send carbon particles into the surrounding tissue and thereby induce unwanted pigmentation. The present invention requires no post-treatment clean-up of the carbon particles. The rupturing of the basement membrane could also result in the infection of the peri-sebaceous gland tissue by P. acnes, itself. Control of the pulse duration in the present invention allows for selective destruction of the targeted sebocytes without rupturing the basement membrane.

Non-monochromatic light can be used if appropriately pulsed and filtered Low energy Xenon flashlamps, when filtered to effectively eliminate light below 900 nm and light above 1300 nm, can be used for selective photothermolysis of sebaceous glands. This is due to the strong absorption of light in this range by sebum and the low absorption of light in this range by other major tissue chromophores. Here, too, control of the pulse duration will allow for selective destruction of the targeted sebecytes without rupturing the basement membrane or inducing thermal damage in the overlying or surrounding tissues.

Selective photothermolysis of sebaceous glands can also be achieved through the use of visible light and the intrafollicular means of delivery. Squalene, a component of sebum, has an absorption peak around 480 nm. Although this wavelength is strongly absorbed by melanin and blood components, if delivery to the sebaceous glands via a hollow waveguide inserted into the follicle is used, damage to non-targeted tissue is minimal. The high angle of divergence of the laser light from the 50–70 micron diameter waveguide eliminates the need to precisely locate the sebaceous gland. Sources producing light near the squalene absorption peak are commercially available. Argon lasers (488 nm), frequency-doubled Nd: YAG lasers (473 nm), as well as frequency-doubled diode lasers (440–490 nm) can be utilized.

The use of light targeting sebum can also be used to treat ringworm and folliculitis. Ringworm is a fungal infection of the follicle. Presently, treatment consists of anti-fungal agents applied topically. Ringworm, due to the site of infection, can be resistant to treatment. By targeting the sebum in the infected follicle, the heat generated can be used to kill the fungus infecting it. Similarly, folliculitis, a general infection of the follicle, can be treated by targeting the sebum in the infected follicle.

The system in accordance with the invention can be comprised of a laser or a filtered, pulsed flashlamp source, a delivery system for delivering the light beam 18 from the source to the target. The delivery system will be composed, in part, of a handpiece from which the light beam will emanate. The handpiece can be either of the non-contact or of the contact variety. Furthermore, if the intrafollicular approach is chosen, the handpiece will have a small diameter probe which is inserted into the sebaceous follicle in order to deliver the visible laser light to the sebaceous gland, by-passing the overlying epidermal and dermal tissues.

The handpiece can be of the contact or the non-contact type. Contact handpieces can be useful if the index of refraction of the wavelength used differs significantly in air and in tissue. Contact handpieces can be used to reduce reflection from the skin surface arising from the difference in index of refraction. Additionally, a contact handpiece can be cooled, further reducing the possibility of damage to the overlying tissues during treatment. Non-contact handpieces have the advantage that no contamination of the handpiece's optical components occurs during the treatment. Therefore, there will be no need to clean those optical surfaces, which are likely to be specially-coated to reduce transmission losses, on a frequent basis.

Figure 1:
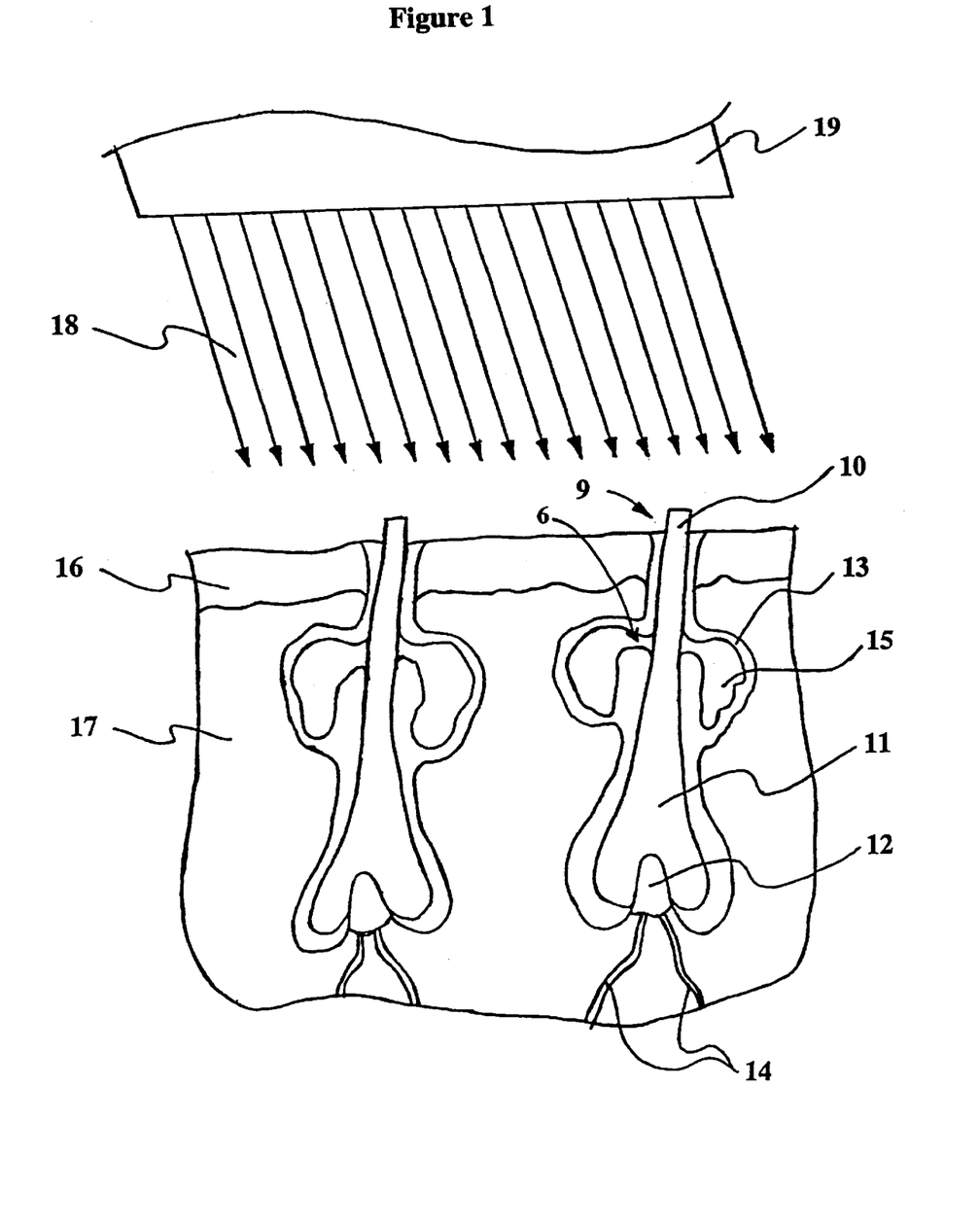
FIG. 1 is a cross-sectional view of human skin, showing the upper layers of the skin, the major structures contained within each, and the laser beam impinging upon the surface of the skin.
Figure 3:
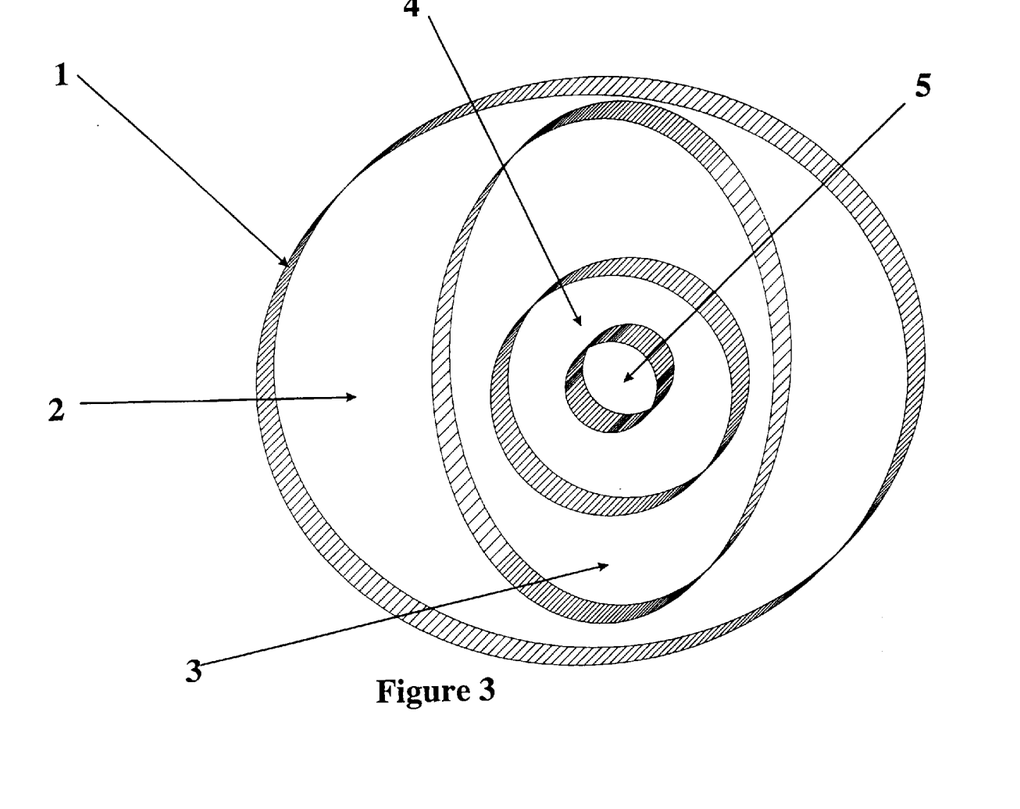
FIG. 3 is the idealized cross-sectional view of a sebaceous saccule, showing the basement membrane, the undifferentiated sebocytes, the differentiated sebocytes, the mature sebocytes, and the sebum, itself.
Figure 4:
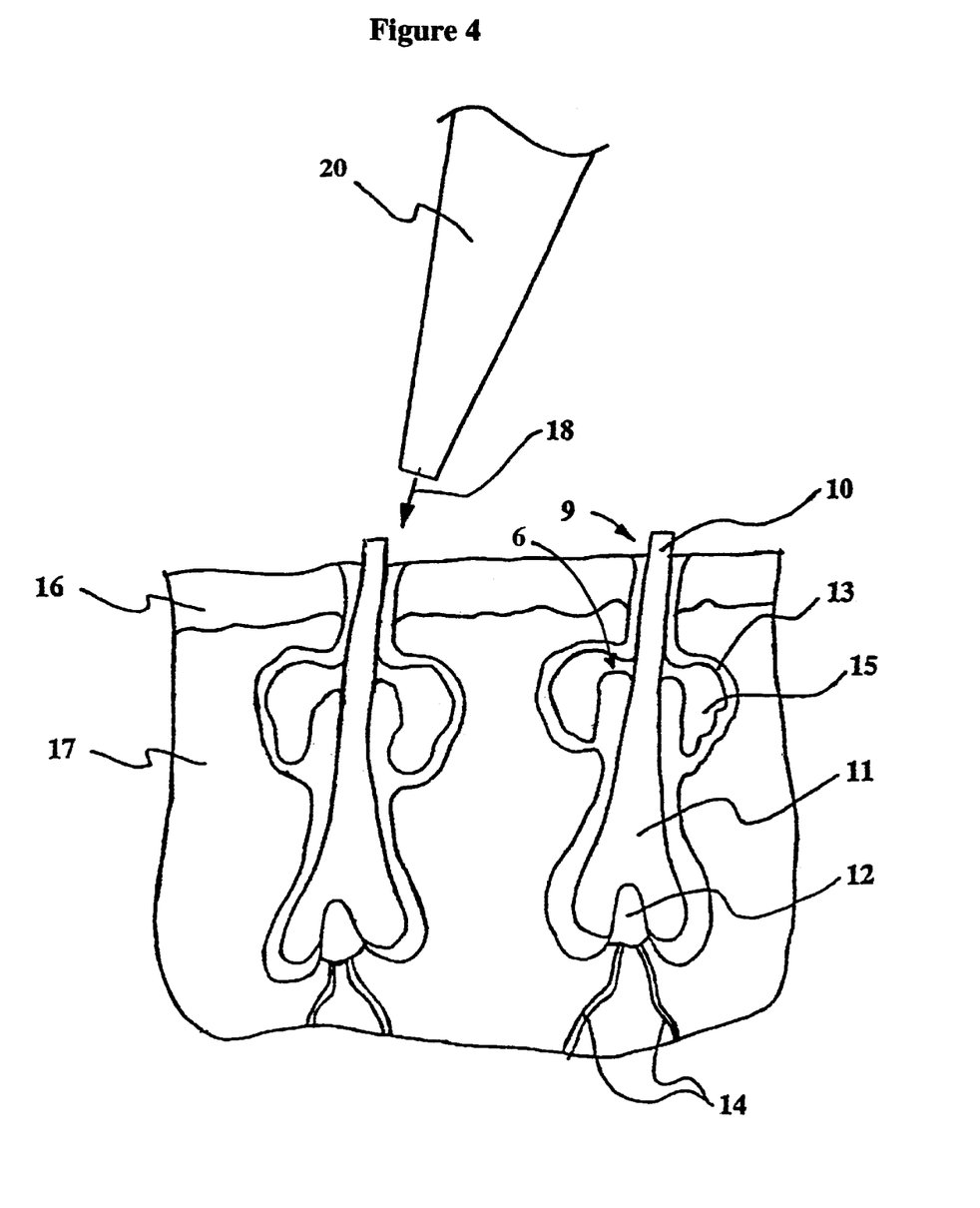
FIG. 4 is a cross-sectional view of human skin, showing the upper layers of the skin, the major structures contained within each, and the intrafollicular probe to be used to deliver visible light at or near an absorption peak of squalene, while by-passing the absorption of said light by melanin and blood components.

As illustrated in FIGS. 1 and 4, the overall target is the sebaceous gland 15. The sebaceous gland 15 as detailed in FIG. 3 further is comprised of a basement membrane 1, undifferentiated cells 2, differentiated cells 3, mature cells 4, sebum 5, and, as seen in FIGS. 1 and 4, a duct 6. The differentiated cells 3, mature cells 4, and sebum 5 are composed in a large part by lipids of one type or another. The other cellular components of the sebaceous gland are typically of high water content and lower lipid content.

As illustrated in FIGS. 1 and 4, the tissue overlying and surrounding the target sebaceous gland is composed of tissues with high melanin content, like the epidermis 6, and tissues with high water and/or hemoglobin content, like the dermis 17.

Therefore the major biological events involved with the present invention can be summarized as follows:
1) the sebum (i.e., keratin and lipids) in the gland, as well as the lipids in the mature and differentiated sebocytes, is heated by absorption of light. The heating kills these sebocytes, causing the Type I 5 ampha-reductase activity to cease.
2) The cessation of the metabolization of T into DHT reduces a) the proliferation of undifferentiated sebocytes, and b) the differentiation of existing undifferentiated sebocytes.
3) The destroyed differentiated and mature serscytes cease functioning as "lipid factories".
4) Rate of sebum production is reduced dramatically and for an extended period of time.
5) Access to DHT in the circulating blood eventually result s in the differentiation of undifferentiated sebocytes, which in turn begin to metabolize DHT from T. The cycle begins anew.
6) The patient is treated again.

Figure 5:
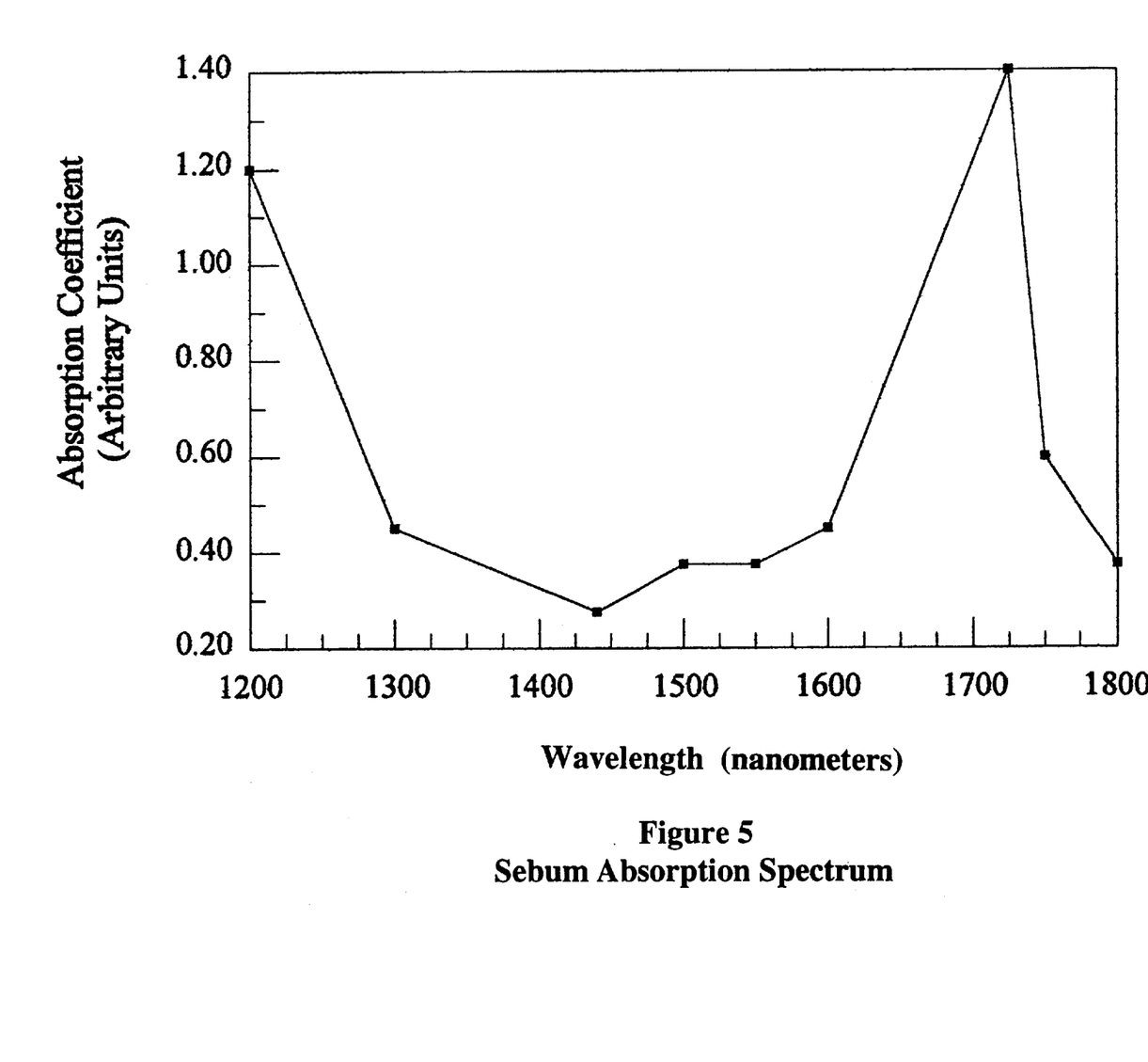
FIG. 5 is the absorption spectra of sebum in the near IR-to- mid IR portion of the electromagnetic spectrum.

In accordance with one embodiment of the invention, the wavelength employed by the laser is chosen in order to minimize light absorption by the epidermis and dermis while delivering energy to the targeted sebocytes. As illustrated in FIG. 2, some wavelengths in the 900–1350 range have relatively low absorption by melanin, blood components, and several other tissue cliromophores. This is also true in the 1600–1750 nm range. In the 1600–1750 nm range, however, water absorption may limit the effectiveness of the approach to acne prevention. Additionally, as illustrated in FIG. 2, the absorption of sebum in the 900–950 nm, 1200–1350 nm, and (see FIG. 5) 160–1750 mn ranges is high, relative to that of water, melanin, blood components, and other major tissue chromophores, in the specified wavelength ranges.

In accordance with one embodiment of the invention, the wavelength employed by the laser is chosen to maximize the light absorption by the squalene component of the sebum. The delivery means includes a small diameter (50–70 microns) waveguide which is inserted into the follicle allowing the light to irradiate the sebaceous glands with little or no absorption by the melanin in the soft tissue or by blood components.

TABLE 1

Lipid Composition of sebum, in-vivo (Note: Keratin is an important component of sebum.)

| Component | % Isolated gland |
|---|---|
| Triglycerides | 57 |
| Wax Esters | 25 |
| Squalene | 15 |
| Cholesterol esters | 2 |
| Cholesterol | 1 |

Furthermore, in accordance with the invention, I claim:

1. A method for reducing the rate of production of sebum by the sebaceous glands of the human skin by means of the use of pulsed laser light and a delivery system, said method comprising the steps of: providing pulsed laser light having a wavelength which passes through the skin with minimal absorption by the surrounding and overlying tissues and which is substantially absorbed by the lipid component of the sebum and the targeted mature and differentiated sebocytes; providing said delivery system which directs said pulsed laser light onto the surface of said skin; and directing said laser light onto the surface of said skin for a period of time sufficient to cause photocoagulation of said targeted mature and differentiated sebocytes.

2. The method of claim 1, wherein said wavelength of laser light is between 900–950 nanometers.

3. The method of claim 1, wherein said wavelength of laser light is between 1200–1350 nanometers.

4. The method of claim 1, wherein said wavelength of laser light is between 1600–1750 nanometers.

5. The method of claim 1, wherein the duration of the pulse of said laser light is between 10 milliseconds and b 0.5 seconds, in order to optimize the heat retained by the sebaceous gland while minimizing damage to surrounding tissue.

6. The method of claim 1, wherein the intensity of the pulse of said laser light is chosen to allow photocoagulation of said targeted sebocytes.

7. The method of claim 1, wherein said delivery system is in part composed of a non-contact handpiece.

8. The method of claim 1, wherein said delivery system is in part composed of a contact handpiece.

9. A method for treating ringworm-infected follicles or folliculitis in the human skin by means of the use of pulsed light and a delivery system, said method comprising the steps of: providing pulsed light having a wavelength which passes through the skin with minimal absorption by the surrounding and overlying tissues and which is substantially absorbed by the lipid component of the sebum; providing said delivery system which directs said pulsed laser light onto the surface of said skin; and directing said pulsed laser light onto the surface of said skin for a period of time sufficient to cause thermal destruction of the infecting fungus or other micro-organisms by the heat conducted from the sebum while sparing permanent damage to the surrounding tissue.

10. The method of claim 9, wherein the duration of the pulse of said light is between 10 milliseconds and 0.5 seconds, in order to optimize the heat retained by the follicle while minimizing damage to surrounding tissue.

11. The method of claim 9, wherein the intensity of the pulse of said light is chosen to allow thermal destruction of the infecting fungus.

12. The method of claim 9, wherein said wavelength of said light is between 900–950 nanometers.

13. The method of claim 9, wherein said wavelength of said light is between 1200–1350 nanometers.

14. The method of claim 9, wherein said wavelength of said light is between 1600–1750 nanometers.

15. The method of claim 9, wherein said delivery system is in part composed of a non-contact handpiece.

16. The method of claim 9, wherein said delivery system is in part composed of a contact handpiece.

17. A method for reducing the rate of production of sebum by the sebaceous glands of the human skin by means of the use of pulsed laser light and a delivery system, said method comprising the steps of: providing pulsed laser light being delivered to the sebaceous gland in a way so as to avoid absorption by the melanin and blood components in the overlying tissue and which is substantially absorbed by the squalene component of the sebum and the targeted mature and differentiated sebocytes; providing said delivery system which directs said pulsed laser light onto the surface of said skin; and directing said laser light onto the sebaceous gland for a period of time sufficient to cause photocoagulation of said targeted mature and differentiated sebocytes.

18. The method of claim 17, wherein said wavelength of laser light is between 400–550 nanometers.

19. The method of claim 17, wherein the duration of the pulse of said laser light is between 10 milliseconds and 0.5 seconds, in order to optimize the heat retained by the sebaceous gland while minimizing damage to surrounding tissue.

20. The method of claim 17, wherein the intensity of the pulse of said laser light is chosen to allow photocoagulation of said targeted sebocytes.

21. A method for reducing the rate of production of sebum by the sebaceous glands of the human skin by means of the use of pulsed and filtered non-monochromatic light and a delivery system, said method comprising the steps of: providing pulsed and filtered non-monochromatic light being in a range of wavelengths which passes through the skin with minimal absorption by the surrounding and overlying tissues and which is substantially absorbed by the lipid component of the sebum and the targeted mature and differentiated sebocytes; providing said delivery system which directs said pulsed and filtered non-monochromatic light onto the surface of said skin; and directing said light onto the surface of said skin for a period of time sufficient to cause photocoagulation of said targeted mature and differentiated sebocytes.

22. The method of claim 21, wherein said wavelength of said light is between 900–1300 nanometers.

23. The method of claim 21, wherein said wavelength of said light is between 1600–1750 nanometers.

24. The method of claim 21, wherein the duration of the pulse of said light is between 10 milliseconds and 0.5 seconds, in order to optimize the heat retained by the sebaceous gland while minimizing damage to surrounding tissue.

25. The method of claim 21, wherein the intensity of the pulse of said light is chosen to allow photocoagulation of said targeted sebocytes.

26. The method of claim 21, wherein said delivery system is in part composed of a non-contact handpiece.

27. The method of claim 21, wherein said delivery system is in part composed of a contact handpiece.

* * * * *